United States Patent
Limbrick et al.

(10) Patent No.: US 8,196,483 B2
(45) Date of Patent: Jun. 12, 2012

(54) SYSTEMS AND METHODS FOR EVALUATING MEDICATION DELIVERY FROM VALVED HOLDING CHAMBERS WITH A FACEMASK USING A MODEL FACE

(75) Inventors: Myles Limbrick, London (CA); Robert Morton, London (CA); Mark Nagel, Mt. Brydges (CA); Jolyon Mitchell, London (CA); Peter Gubbels, London (CA); Kimberly Wiersema, Strathroy (CA); Cathy Doyle, London (CA); Valentina Avvakoumova, London (CA)

(73) Assignee: Trudell Medical International, Ontario (CA)

( * ) Notice: Subject to any disclaimer, the term of this patent is extended or adjusted under 35 U.S.C. 154(b) by 446 days.

(21) Appl. No.: 12/326,450

(22) Filed: Dec. 2, 2008

(65) Prior Publication Data

US 2009/0173173 A1    Jul. 9, 2009

Related U.S. Application Data

(60) Provisional application No. 61/005,740, filed on Dec. 7, 2007.

(51) Int. Cl.
*G01D 21/02* (2006.01)

(52) U.S. Cl. ...................................... 73/866.4
(58) Field of Classification Search .............. 73/866.4
See application file for complete search history.

(56) References Cited

U.S. PATENT DOCUMENTS

| 4,796,467 A | 1/1989 | Burt et al. |
| 5,289,819 A | 3/1994 | Kroger et al. |
| 5,808,182 A | 9/1998 | Stumpf |
| 5,823,787 A * | 10/1998 | Gonzalez et al. ............. 434/265 |
| 6,425,395 B1 | 7/2002 | Brewer et al. |
| 2007/0193339 A1 | 8/2007 | Selim et al. |
| 2009/0285763 A1 | 11/2009 | Finlay et al. |

OTHER PUBLICATIONS

PCT—International Search Report for PCT/IB2008/003371, filed on Dec. 5, 2008 (4 pgs.).
PCT—Written Opinion of the International Searching Authority for PCT/IB2008/003371, filed on Dec. 5, 2008 (5 pgs.).

* cited by examiner

*Primary Examiner* — Hezron E Williams
*Assistant Examiner* — Paul West
(74) *Attorney, Agent, or Firm* — Brinks Hofer Gilson & Lione

(57) ABSTRACT

Systems and methods for evaluating medication delivery from valved holding chambers (VHCs) with a facemask using a model face of a child or a model face of an infant are disclosed. Generally, the model face includes a base, an elastomer cast, an air pocket, and a mouth opening. The elastomer cast is positioned on at least a portion of a top of the base. The elastomer simulates soft tissues in a face and defines at least a nose, a chin, and a mouth sized to simulate a nose, a chin, and a mouth of a child. The air pocket is positioned between the base and the elastomer case below at least the nose, the chin, and the mouth of the elastomer cast. The mouth opening defines a passageway through the base, the air pocket, and the mouth of the elastomer cast.

16 Claims, 17 Drawing Sheets

FACE PLATE [X1]

SYSTEMS AND METHODS FOR EVALUATING MEDICATION DELIVERY FROM VALVED HOLDING CHAMBERS WITH A FACEMASK USING A MODEL FACE

BACKGROUND

The present application claims priority to U.S. Provisional Patent App. No. 61/005,740, filed Dec. 7, 2007, the entirety of which is hereby incorporated by reference.

BACKGROUND

Valved holding chambers (VHCs) are used in conjunction with pressurized metered-dose inhalers (pMDIs) to deliver medication via a facemask to a patient. The testing of VHCs is often complicated by the need to achieve a seal between a facemask and a test apparatus. Small leakages between a facemask and test apparatus are known to result in large decreases in delivery efficiency of medication. For this reason, some existing standards recommend removal of a facemask during testing of VHCs. However, a solution for testing VHCs that more closely mimics reality with the use of a facemask and a face is desirable. The realism with the use of a facemask and a face is desirable to simulate an accurate amount of dead space when the facemask is applied to the face.

DETAILED DESCRIPTION OF THE DRAWINGS

The following disclosure is directed to systems and methods for evaluating medication delivery from valved holding chambers (VHCs) with a facemask using a model face of a child or a model face of an infant. The disclosed model faces of a child and an infant simulate the soft tissues of a facial area that typically engages a facemask so that when the model faces are mounted on a testing cradle, a facemask may be applied to the model face at a clinically appropriate orientation with an amount of clinically appropriate force. A seal between the facemask and the model face may then be tested by measuring a flow rate entering the facemask and a flow rate exiting a mouth opening of the model face.

Additionally, a medication delivery from a VHC may be evaluated by delivering aerosolized medication into the facemask and measuring an amount of medication received at the mouth opening of the model face. Alternatively, a medication delivery from a VHC may be evaluated by measuring aerodynamic particle size distribution of medication by transferring an aerosol from the lips of the model face, via a USP/Ph.Eur induction port or similar entry point simulating the human upper airway, to a multi-stage cascade impactor.

Figure 1:
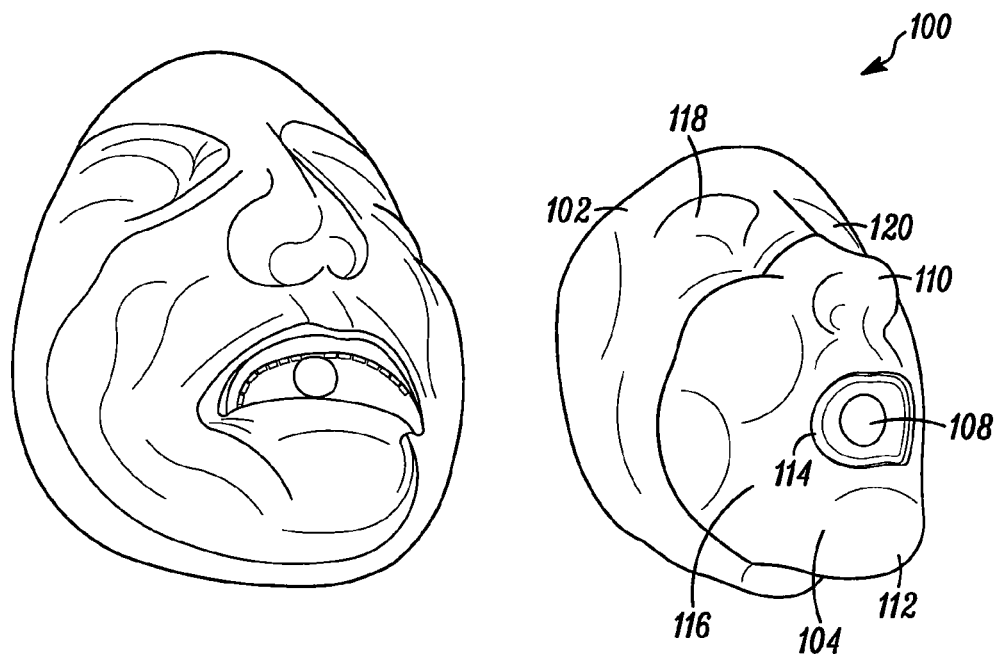
FIG. 1 is a front view of an embodiment of a model face of a child.
Figure 2:
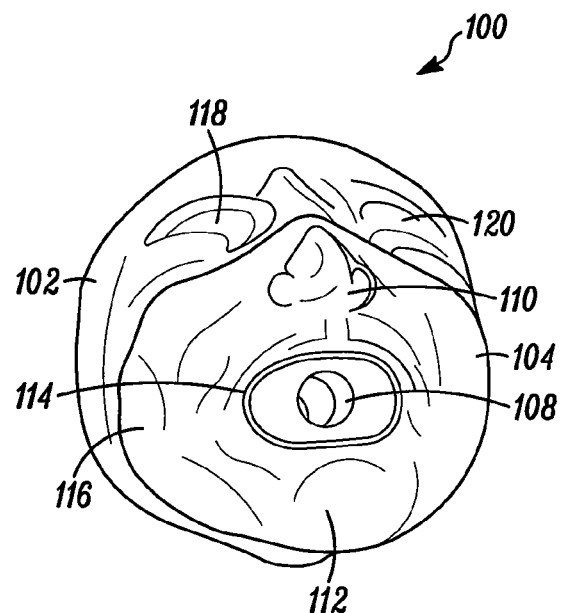
FIG. 2 is a front view of an embodiment of a model face of an infant.

FIG. 1 illustrates a font view of a model face of a child and FIG. 2 illustrates a front view of a model face of an infant. As described in more detail below, the structure of the model face of a child and the model face of an infant may be the same, but the dimensions of the model face of a child and the model face of an infant are different to properly simulate the face of a child and the face of an infant. Generally, a model of a child face simulates a child of ages approximately two to three years, and a model of an infant face simulates an infant of ages approximately nine to twelve months.

A model face 100 may include a base 102, an elastomer cast 104, an air pocket 106, and a mouth opening 108. The elastomer cast 104 is positioned on top of at least a portion of the base 102 and may comprise an elastomer of Shore hardness 10. As described in more detail below, the air pocket 106 is positioned between at least a portion of the base 102 and the elastomer cast 104.

The mouth opening 108 defines a passageway through the base 102, the elastomer cast 104, and the air pocket 106. In one implementation, the mouth opening 108 is sized so that it may be coupled with a USP/Ph.Eur Induction port.

As shown in FIGS. 1 and 2, to simulate the face of a child or an infant, the elastomer cast 104 may define a nose 110, a chin 112, a mouth 114 around the mouth opening 108, and a pair of cheeks 116, and the base 102 may define a pair of eyes 118 and a brow 120. Because of the elastomer of the elastomer cast 104, soft tissues are simulated around the nose 110, chin 112, and mouth 114 area of the face for use in testing a seal between a facemask and the simulated face.

Figure 3:
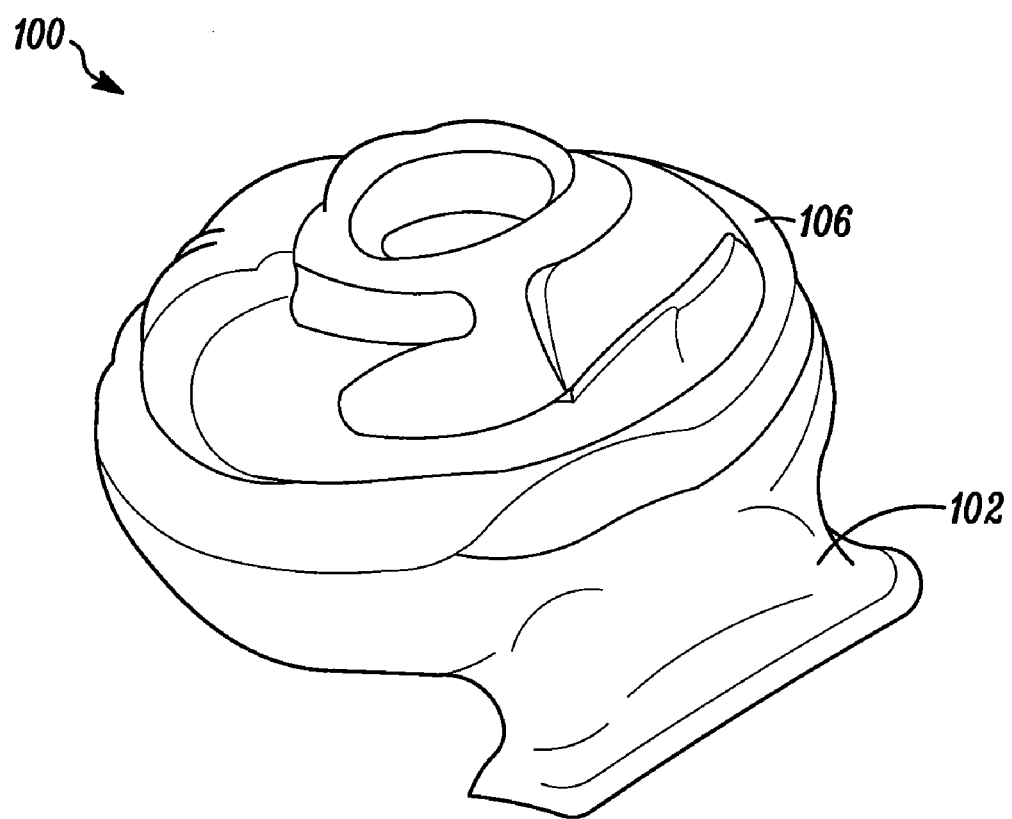
FIG. 3 is an illustration of a cross-section of a model face.

To further simulate soft tissues around the nose 110, chin 112, and mouth 114 area of the face, the air pocket 106 is positioned between the base 102 and the elastomer cast 104 below at least the nose 110, chin 112, and mouth 114 of the elastomer cast 104. Typically the air pocket 106 is of a controlled and fixed depth with a thickness of approximately 0.125 of an inch. FIG. 3 is a diagram of a cross-section of the air pocket 106 positioned on the base 102 and surrounding the mouth opening 108.

Figure 4:
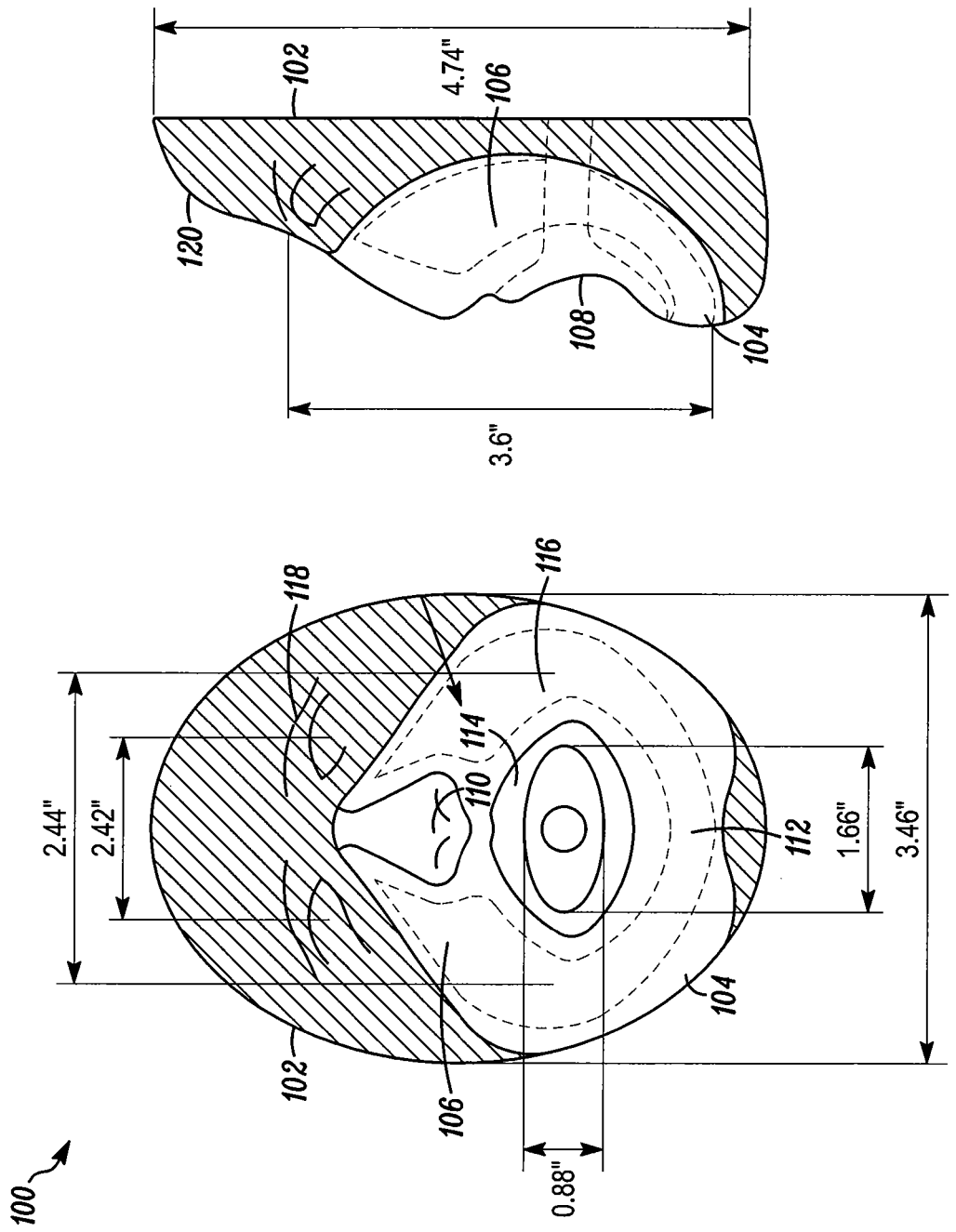
FIG. 4 is a diagram illustrating the dimensions of a model face of a child.

In one implementation, the model face of a child is dimensioned as shown in FIG. 4 with a horizontal distance between a center of each eye 118 substantially equal to 2.62 inches, a horizontal distance between a center of each cheek 116 substantially equal to 2.94 inches, a vertical distance between a center of the chin 112 and a center of the brow 120 substantially equal to 3.6 inches, an overall height of the model face 100 substantially equal to 4.76 inches, and an overall width of the model face substantially equal to 3.46 inches. Further, the mouth opening 108 may have an overall width of approximately 1.66 inches and an overall height of approximately 0.88 of an inch. The elastomer cast 104 may comprise Dow Corning Silastic S, have a shore reading of approximately 10 aerometer, and a wall thickness of approximately 0.125 of an inch. Further, the base 102 may comprise Dow Corning Silastic M-2 with a aerometer of 55 shore A.

Figure 5:
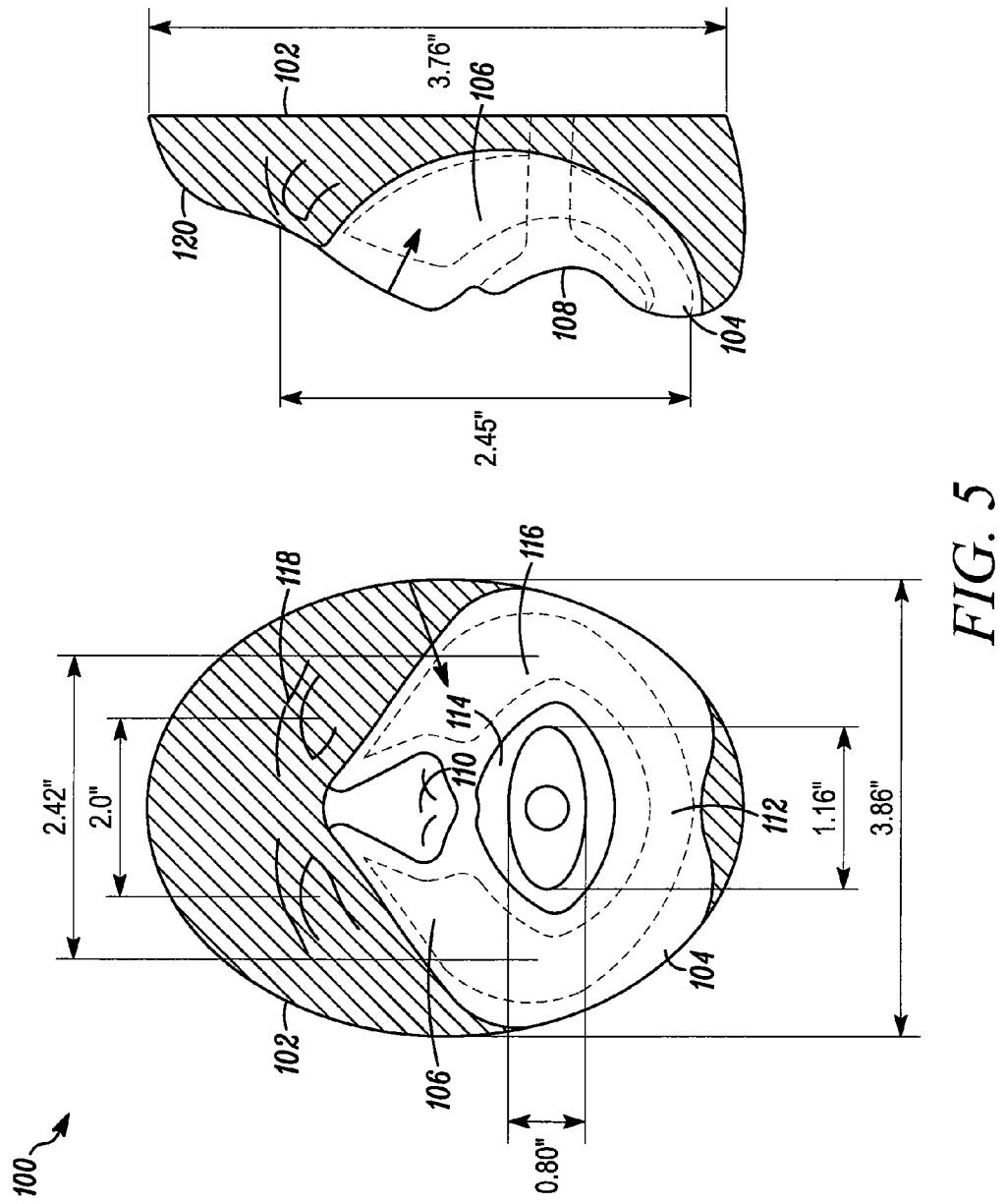
FIG. 5 is a diagram illustrating the dimensions of a model face of an infant.

In another implementation, the model face of an infant is dimensioned as shown in FIG. 5 with a horizontal distance between a center of each eye 118 substantially equal to 2.00 inches, a horizontal distance between a center of each cheek 116 substantially equal to 2.42 inches, a vertical distance between a center of the chin 112 and a center of the brow 120 substantially equal to 2.45 inches, an overall height of the model face 100 substantially equal to 3.76 inches, and an overall width of the model face substantially equal to 3.86 inches. Further, the mouth opening 108 may have an overall width of approximately 1.16 inches and an overall height of approximately 0.80 of an inch. The elastomer cast 104 may comprise Dow Corning Silastic S, have a shore reading of approximately 10 aerometer, and a wall thickness of approximately 0.125 of an inch. Further, the base 102 may comprise Dow Corning Silastic M-2 with a aerometer of 55 shore A.

Figure 6:
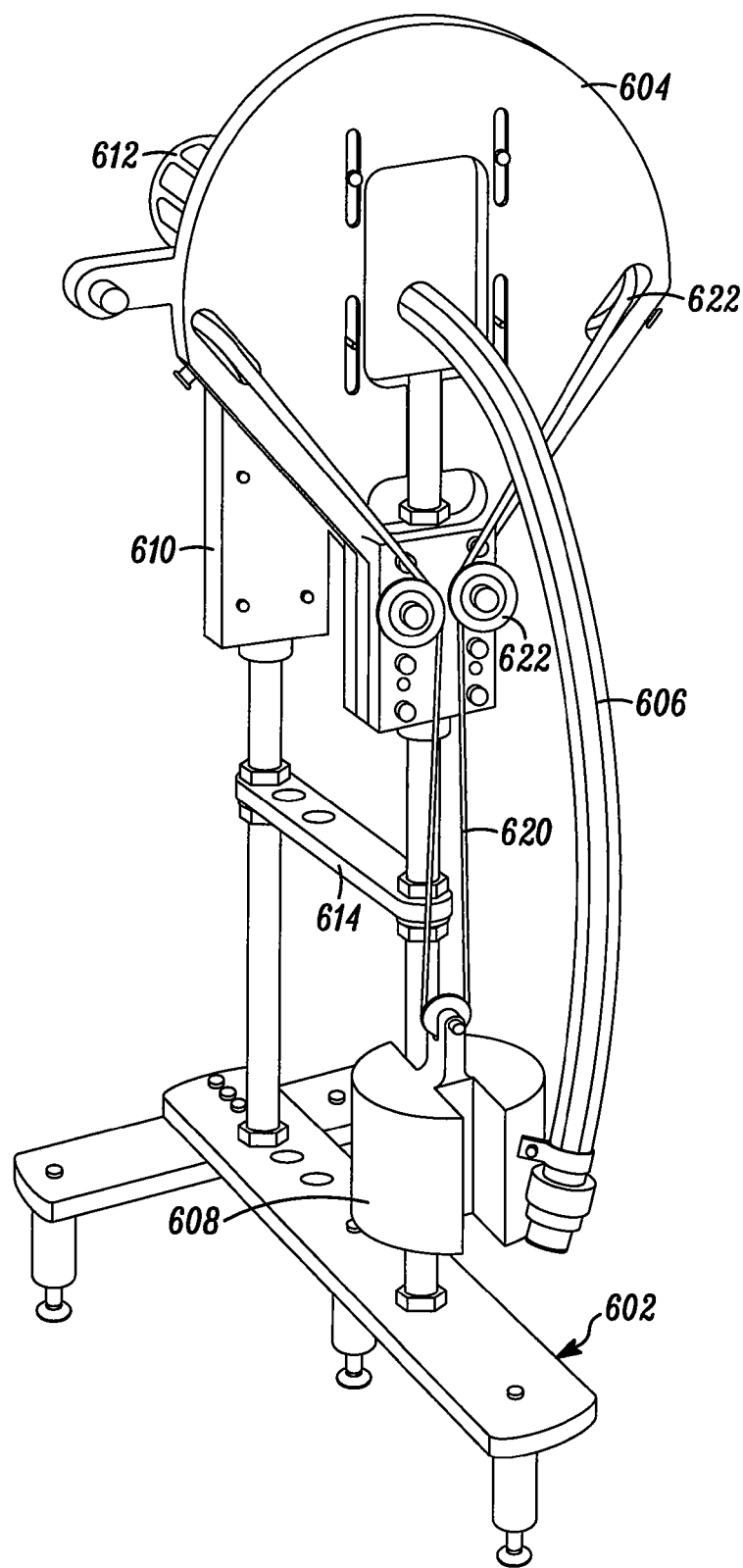
FIG. 6 is a diagram of a testing cradle for use in evaluating the medication delivery from VHCs with a facemask using a model face.
Figure 7:
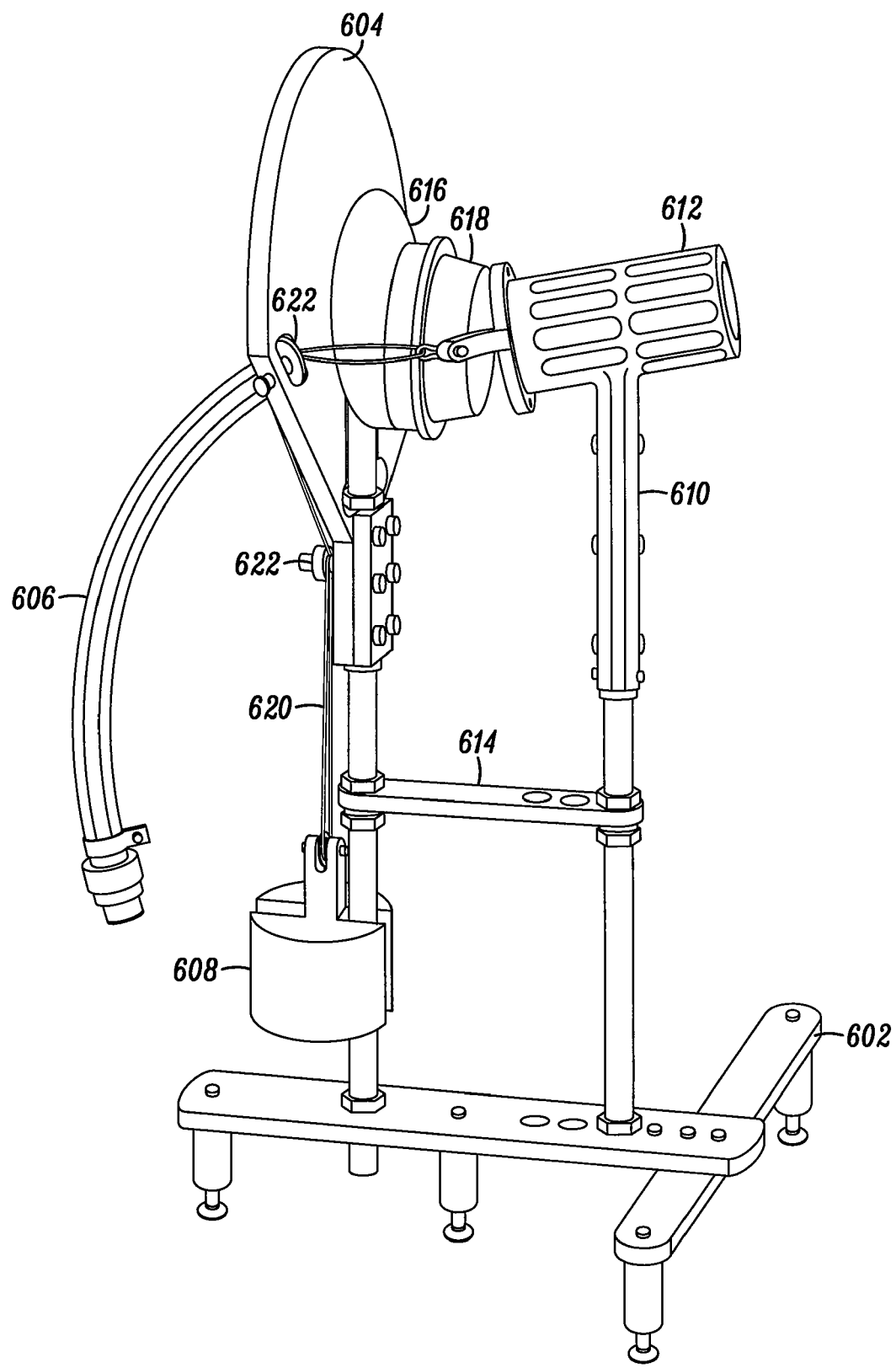
FIG. 7 is a diagram of a testing cradle for use in evaluating the medication delivery from VHCs with a facemask using a model face.
Figure 8:
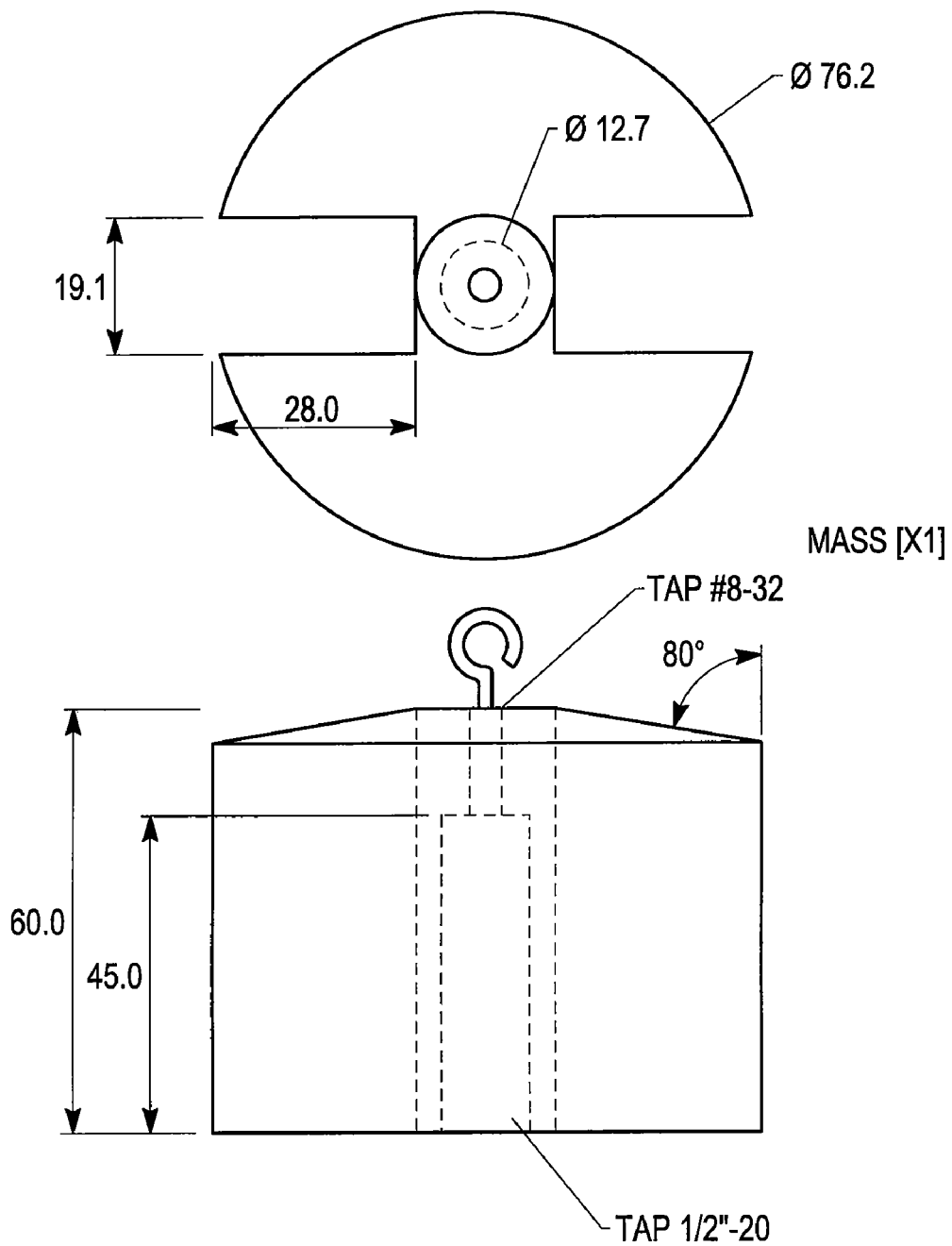
FIGS. 8 through 17 illustrate components of one implementation of a testing cradle such as the testing cradle shown in FIGS. 6 and 7, dimensioned in millimeters.
Figure 9:
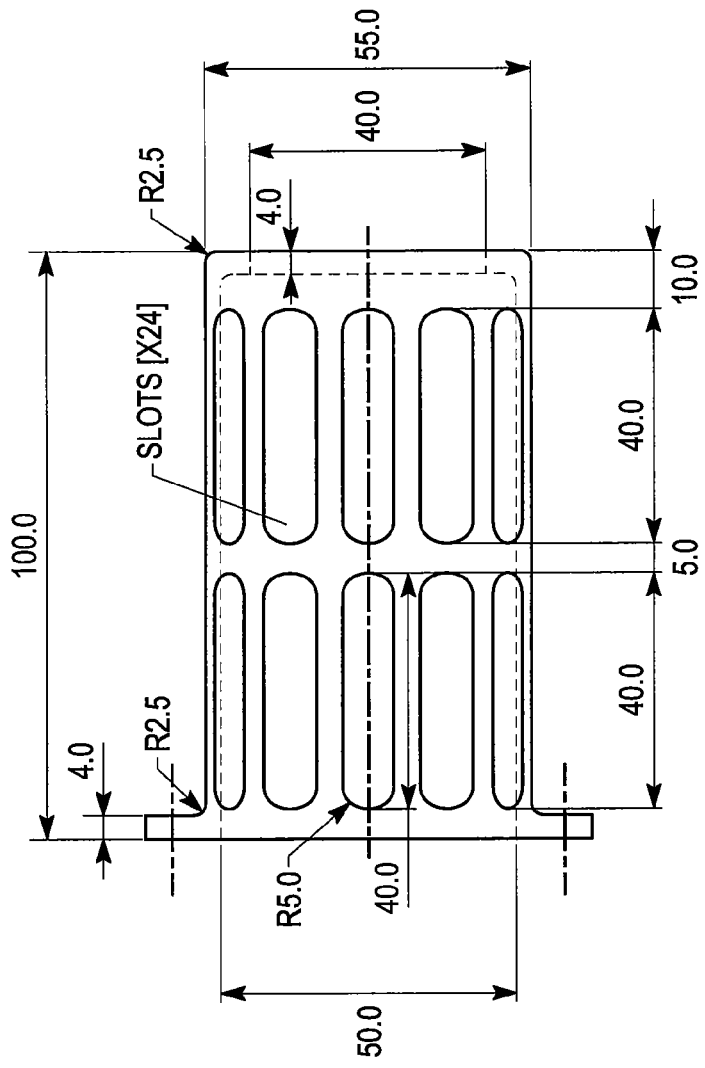
Figure 9:
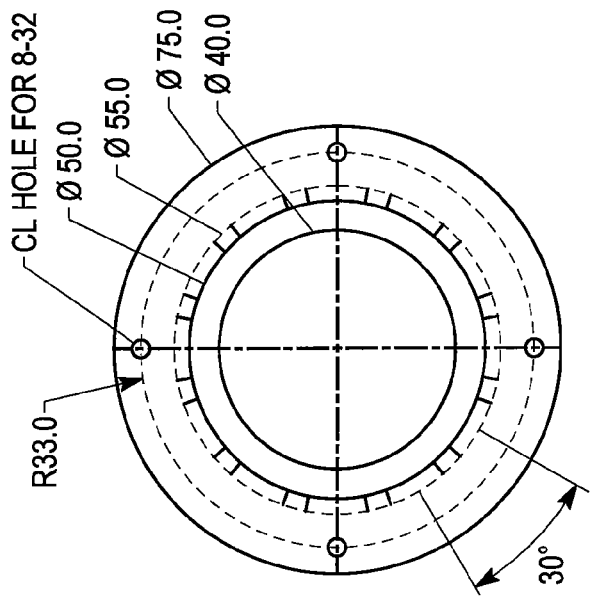
Figure 10:
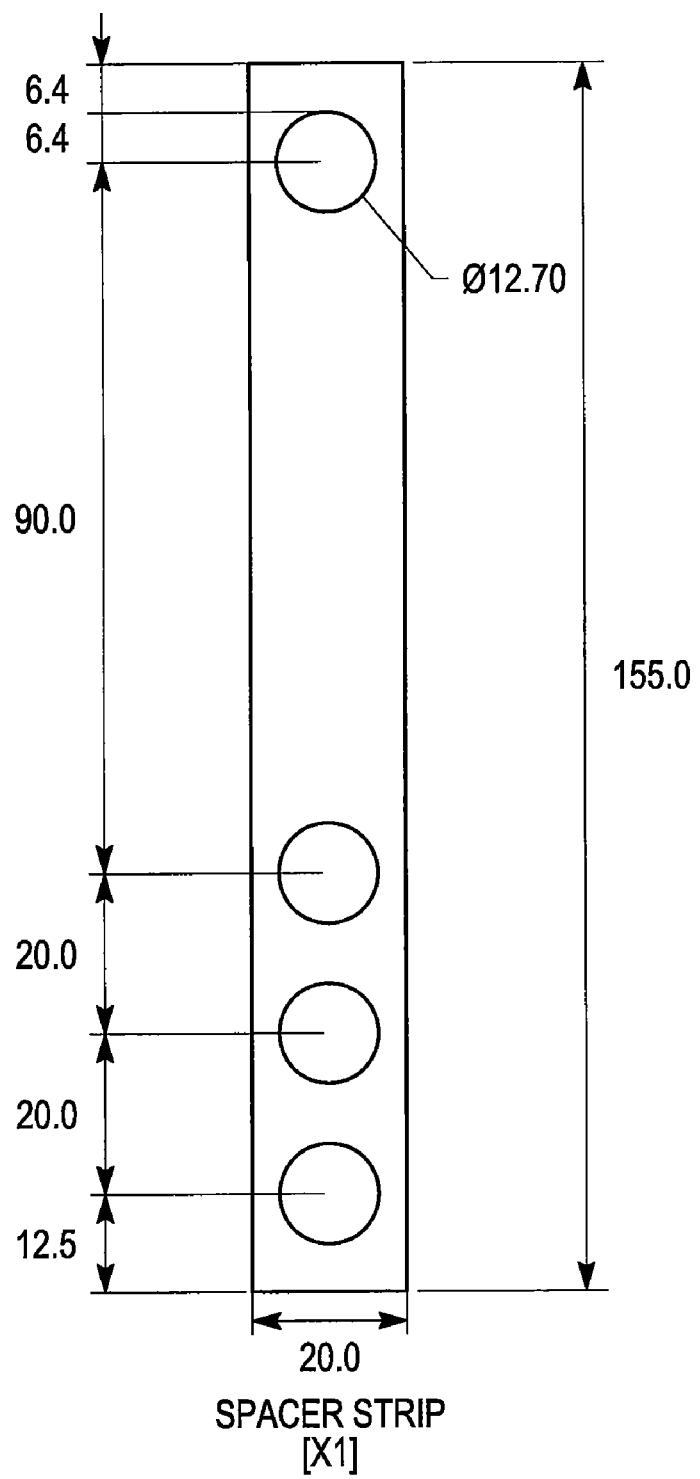
Figure 11:
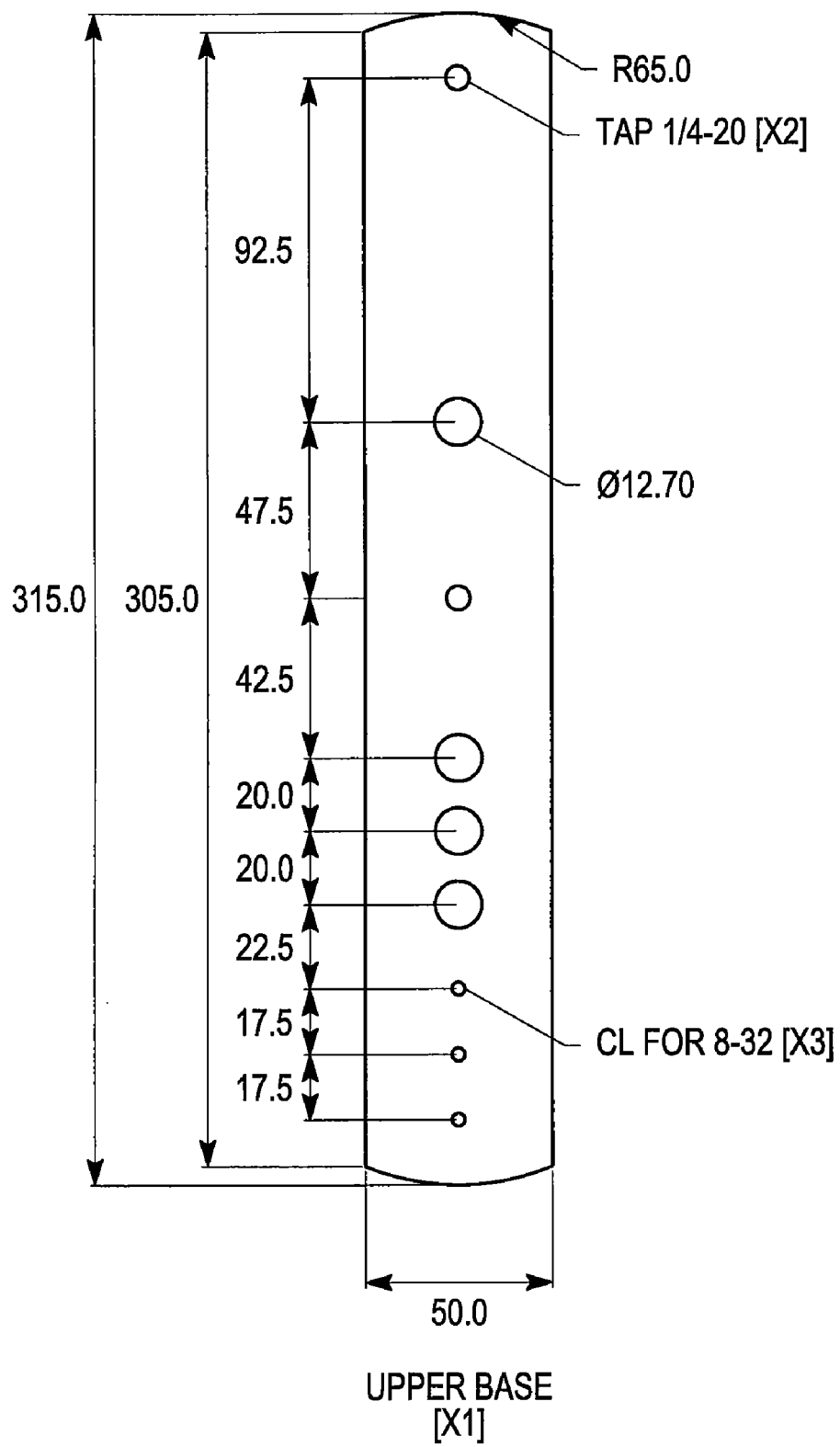
Figure 12:
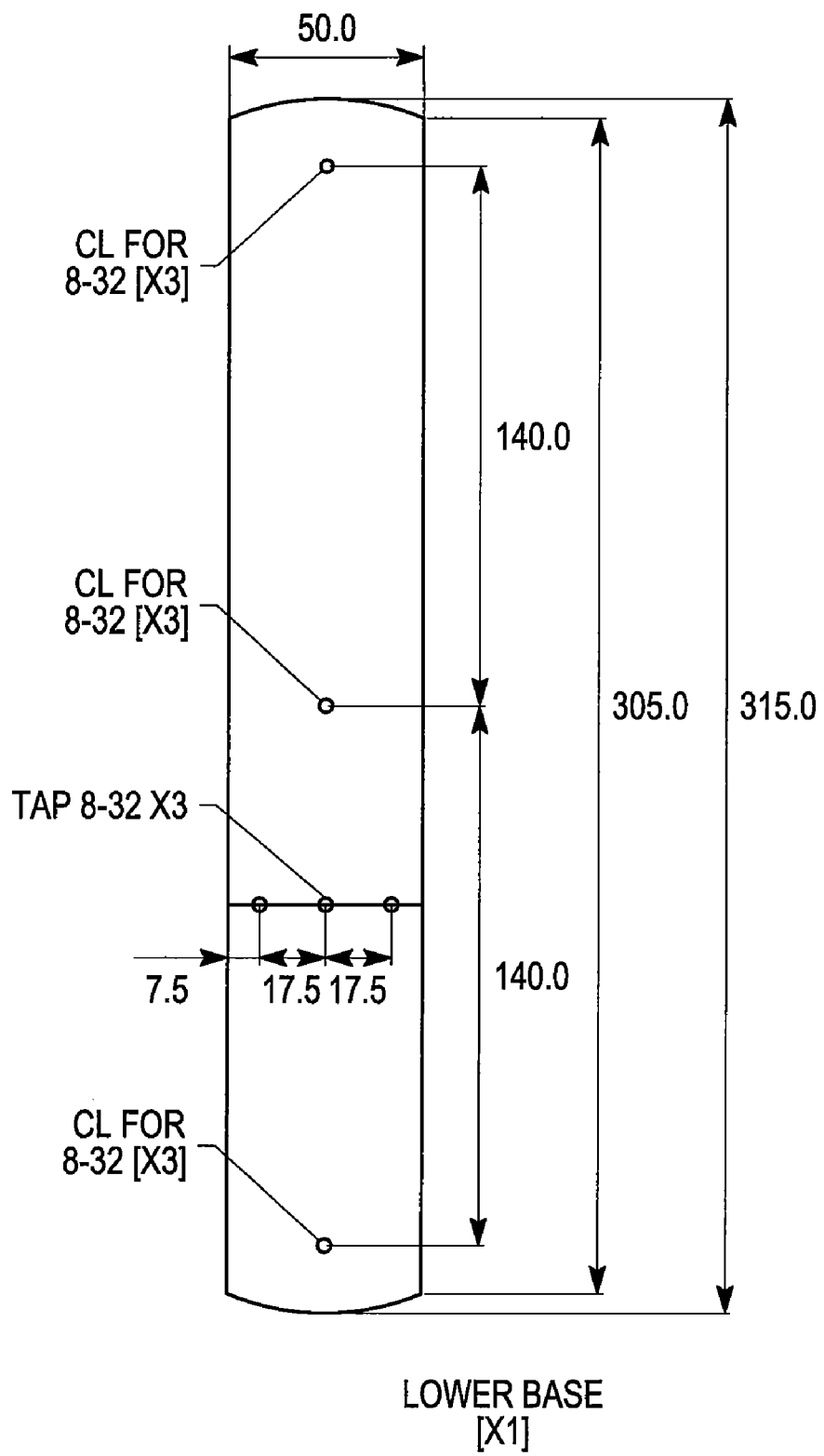
Figure 13:
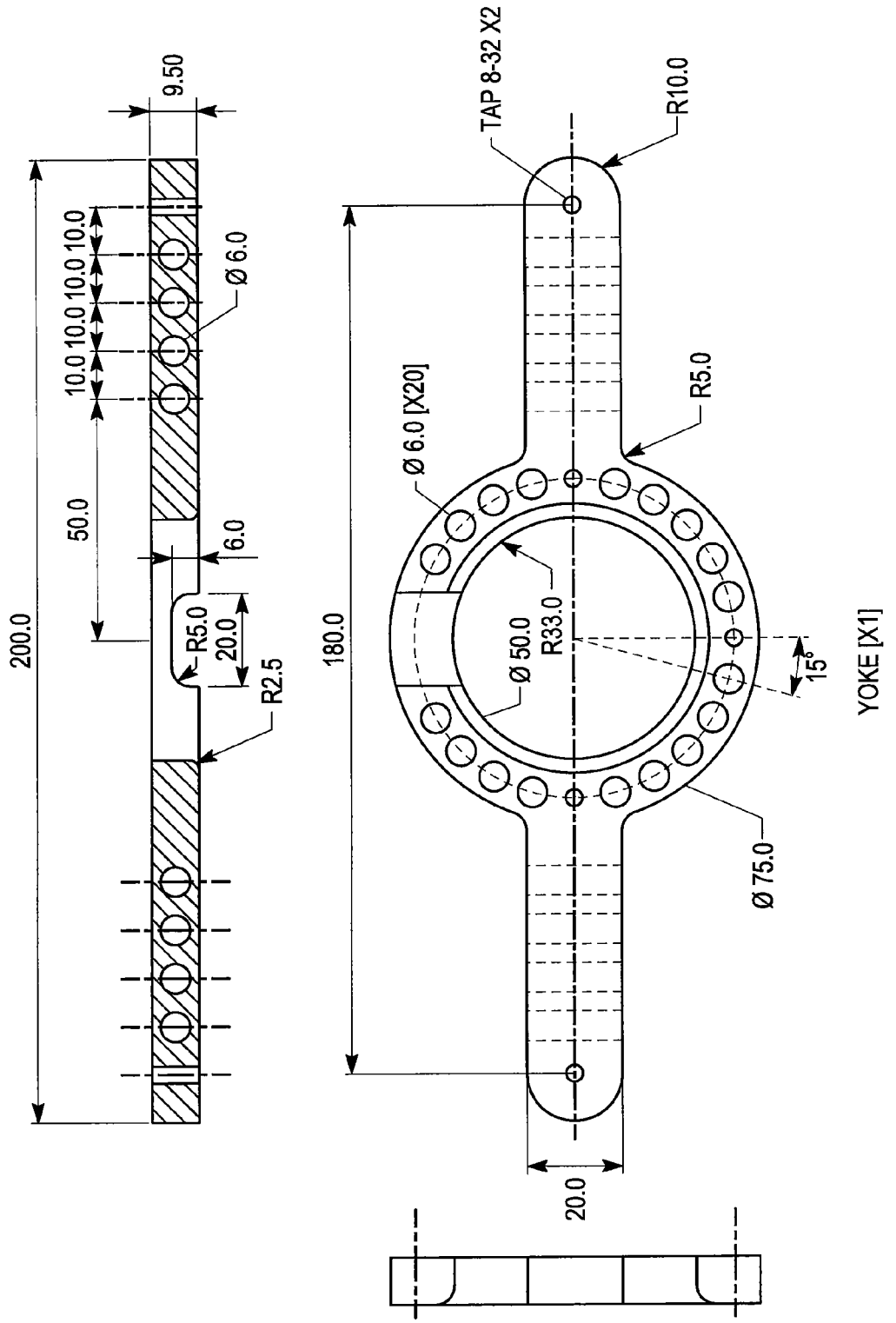
Figure 14:
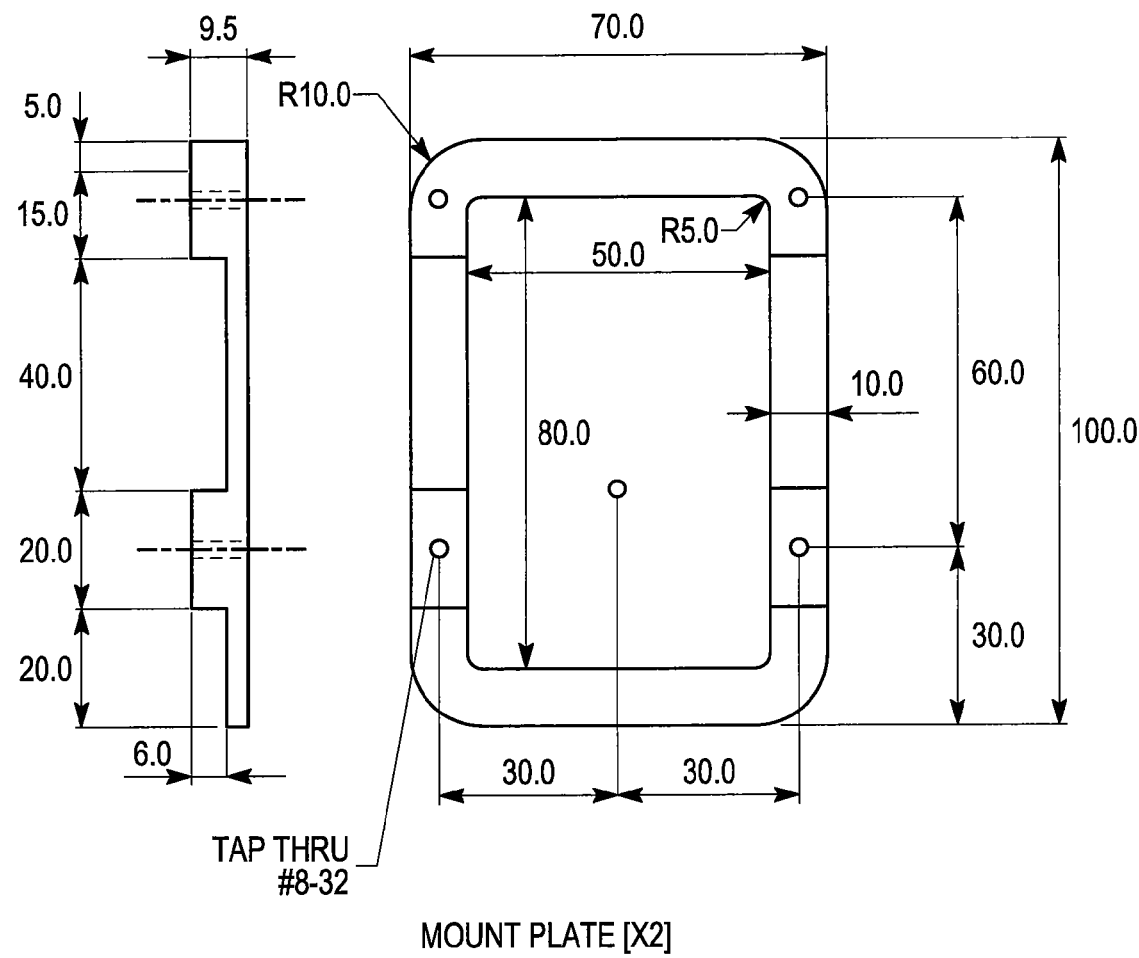
Figure 15:
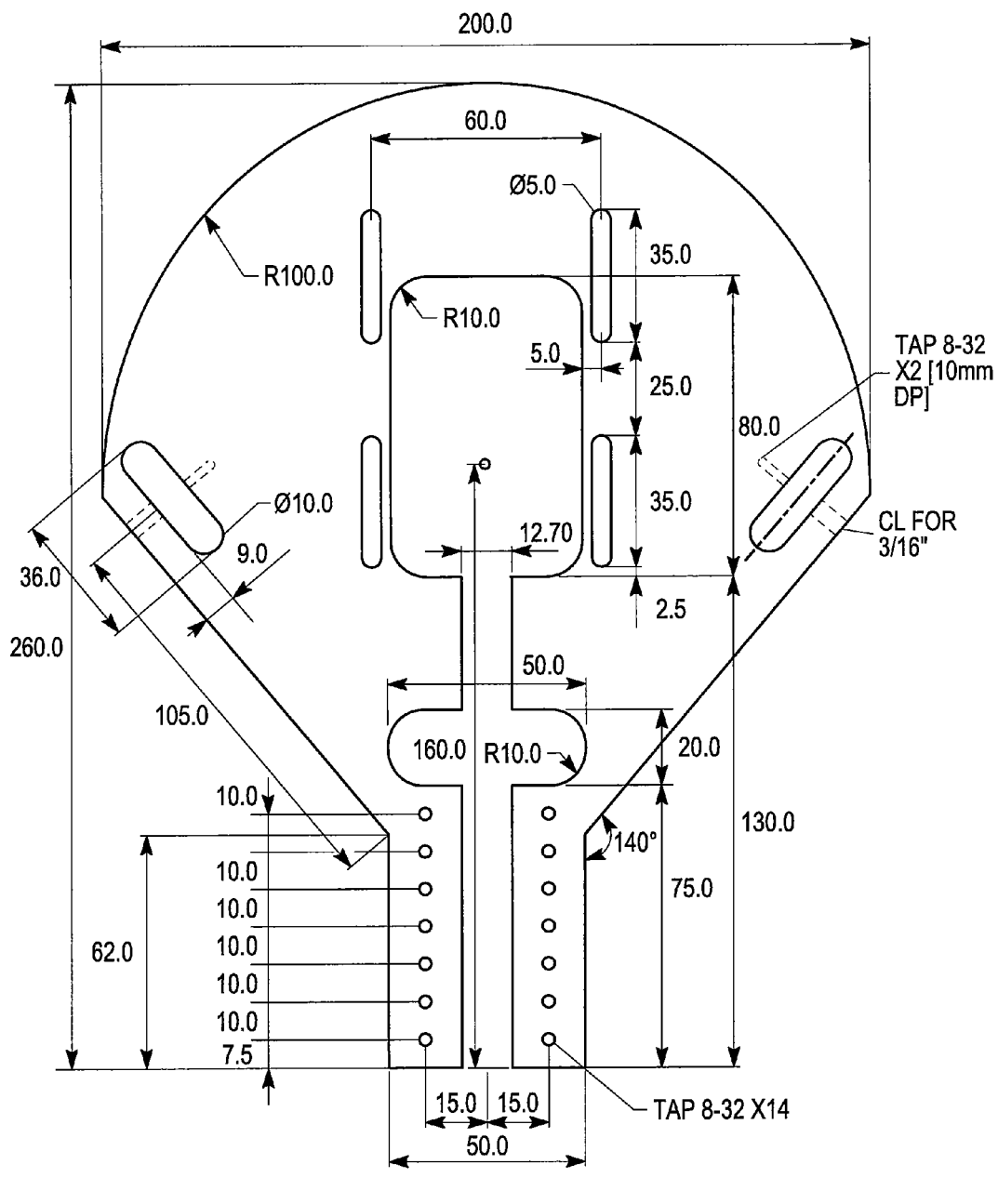
Figure 16:
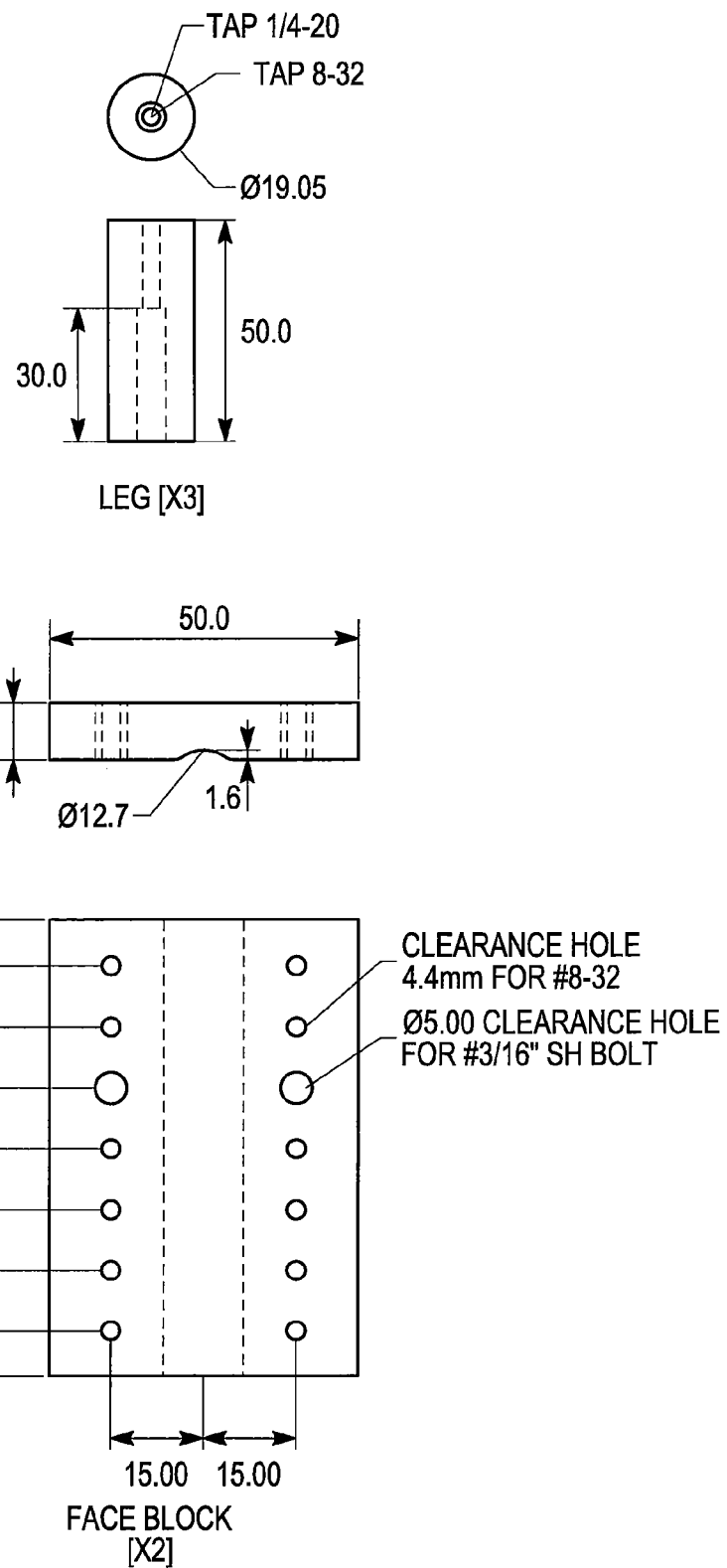
Figure 17:
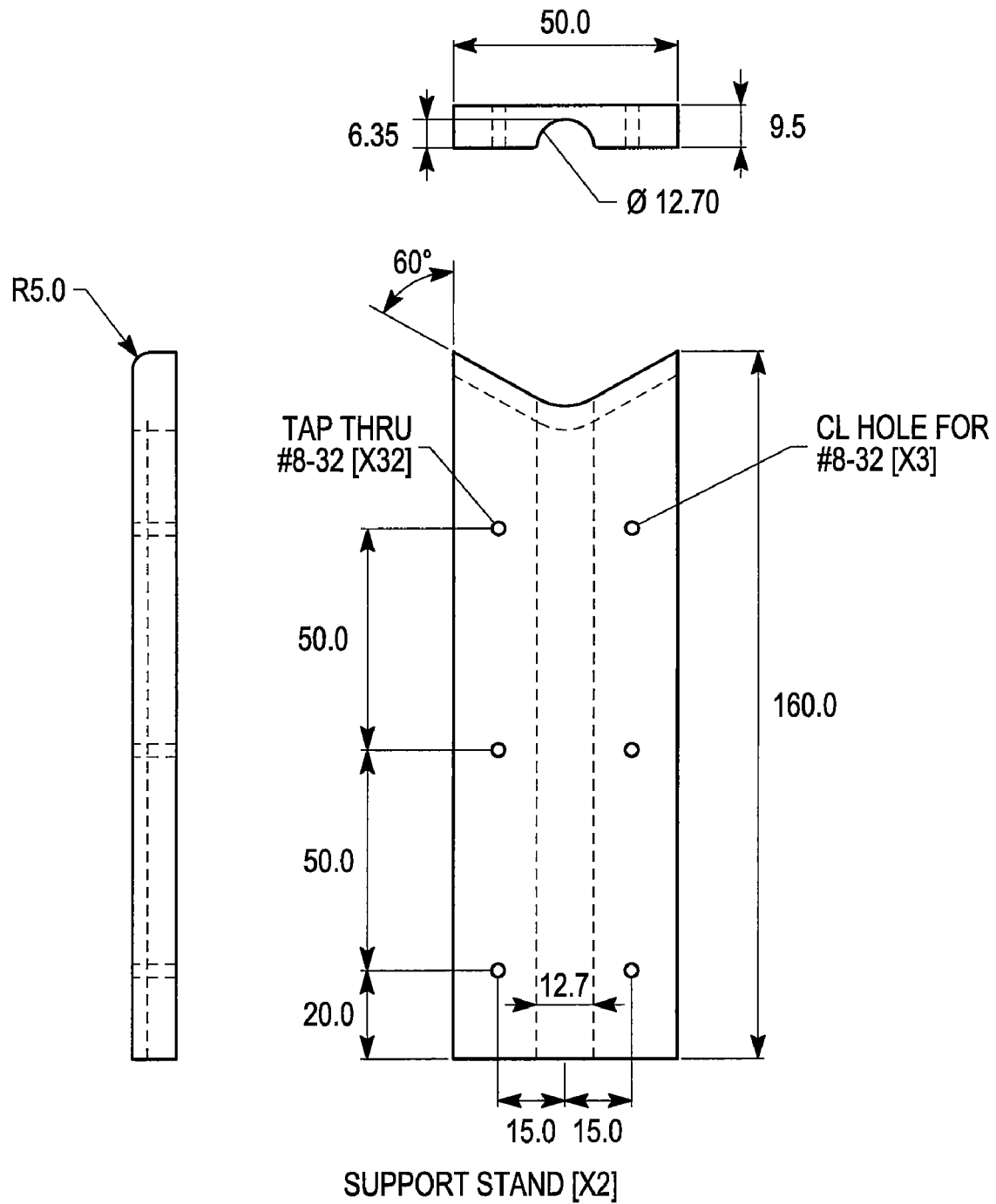

The model faces described above may be mounted on a testing cradle that simulates a clinically appropriate force between a facemask and a model face at a clinically appropriate orientation. The testing cradle may be used to test a seal between a facemask and the simulated face, and to measure an amount of medication received at the mouth opening of the simulated face. FIGS. 6 and 7 are diagrams of one implementation of a testing cradle for use with the model faces described above. Generally, the testing cradle 600 may include a base 602, a faceplate 604, an induction port 606, a weight 608, a support stand 610, a cage 612, and a spacer 614.

The faceplate 604 is fixed to the base 602 and is operative to mount a model face such as those described above in conjunction with FIGS. 1-5. In some implementations, the vertical positioning of the faceplate 604 with respect to the base 602 may be adjusted.

When a model face 616 is mounted on the faceplate 604 as shown in FIG. 7, the induction port 606 couples with, and forms a substantially airtight seal with, the mouth opening of the model face 616 so that gasses may pass through the passageway of the mouth opening into the induction port 606. The indication port 606 may be coupled with various types of testing apparatus for use in simulating the breathing of a patient. For example, when a vacuum is created at the induction port 606, gases or other particulates are drawn into the mouth opening of the model face 616 to simulate a patient inhaling.

It should be appreciated that the induction port 606 may be a USP/Ph.Eur Induction port or equivalent representation of the human oropharynx. The artificial attempt to model the human upper airway (oropharynx) is used when the model face 616 is connected to a multi-stage cascade impactor for measurements of aerodynamic particle sized distribution (APSD) of an inhaled aerosol. The induction port 606 may also be a flexible pipe connection from the model face 616 to a breathing simulator for measurements of emitted total mass of medication, mimicking use by a tidal-breathing patient.

The support stand 610 is pivotly attached to the base 602 such that the support stand 610 may pivot towards the faceplate 604 and the model face 616 mounted on the faceplate 604. The cage 612 is attached to the support stand 610 and is operative to receive a facemask 618 as shown in FIG. 7. When the support stand 610 pivots towards the faceplate 604 and the model face 616, the facemask 618 engages, and forms a seal with, the model face 616. It should be appreciated that when the facemask 618 engages the model face 616, an airflow path is created so that gases may flow from the cage 612 into facemask 618, and then into the induction port 606 via the mouth opening of the model face 616. A flow meter or a pressure measurement device (not shown) may also be coupled with the induction port 606 to measure the gases flowing through the facemask 618 and the mouth opening of the model face 616.

In some implementations, the orientation of the model face 616 with respect to the faceplate 604 may be adjusted vertically, horizontally, and/or angularly, thereby adjusting the position of the model face 616 with respect to the facemask 618 when the facemask 618 engages the model face 616. These adjustments may be made to test both ideal and non-ideal seals between the facemask 618 and the model face 616.

To simulate the amount of force with which the facemask 618 is typically applied to the model face 616 and allow for hands-free operations, the weight 608 creates a force that pulls the support stand 610 towards the faceplate 604. In the implementation of FIGS. 6 and 7, the weight 608 is coupled to the support stand 610 to pull the support stand towards the faceplate 604 via a steel wire 620 and a series of pulleys 622 on the faceplate 604. More specifically, as gravity pulls the weight 608 downward, the steel wire 620 and series of pulleys 622 transfers the force on the weight to the support stand 610, thereby pulling the support stand 610 towards the faceplate 604. In one implementation, the weight is equal to approximately 1.6 kg. However in other implementations, devices other than weights may be used to simulate the clinically appropriate force between the facemask 618 and the model face 618.

As shown in FIGS. 6 and 7, the spacer 614 is typically positioned between the faceplate 604 and the support stand 610 to assist in directing the facemask 618 towards the model face 616.

FIGS. 8 through 17 illustrate components of one implementation of a testing cradle such as those shown in FIGS. 6 and 7, dimensioned in millimeters.

Figure 18:
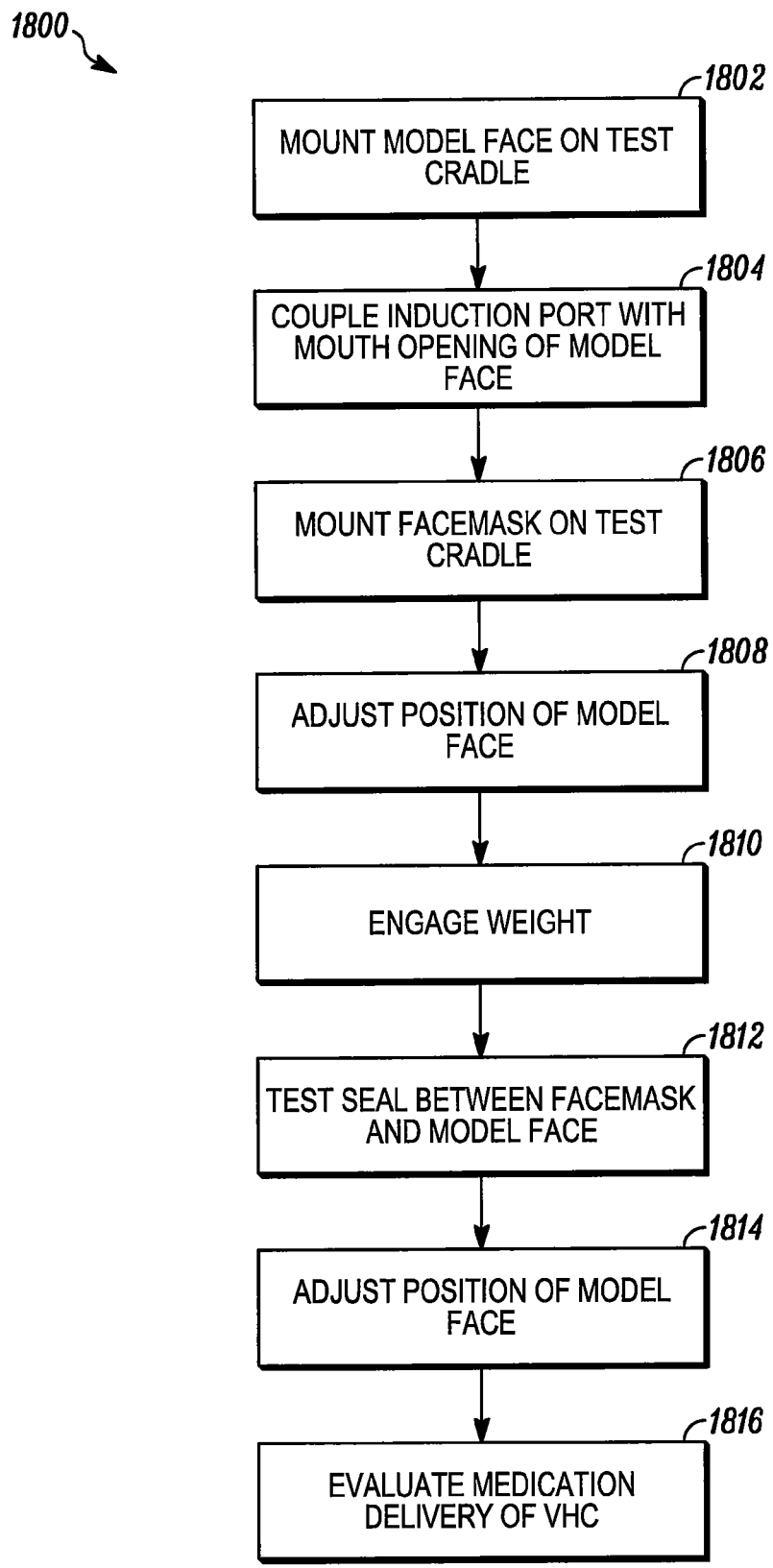
FIG. 18 is a flow chart of a method for evaluating the medication delivery from VHCs with a facemask using a model face.

FIG. 18 is a flow chart of a method for evaluating the medication delivery from VHCs with a facemask and a model face. Generally, the method 800 begins at step 1802 with a model of a face being mounted to a test cradle. When the model of the face is mounted to the test cradle, an induction port Is coupled with a mouth opening of the face at step 1804.

At step 1806, the facemask is mounted on the test cradle, and at step 1808, the horizontal, vertical, and/or angular position of the model face with respect to the faceplate may be adjusted so that the facemask properly engages the model face when the test cradle pivots towards the faceplate. At step 1810, the weight of the test cradle is engaged to create a clinically appropriate force between the facemask and the model of the face.

At step 1812, a seal between the facemask and the model of the face is tested. In one implementation, the seal between the facemask and the model of the face is tested by creating a vacuum to simulate an inhalation at the mouth opening of the model face. The flow rate of gases or particulates entering the facemask and leaving the mouth opening is then measured, and based on the difference in flow rates, a quality of the seal can be determined. It will be appreciated that the closer a difference in a flow rate of gases or particulates entering the facemask and a flow rate of gases or particulates leaving the mouth opening is to zero, the better the seal between the facemask and the model of the face. At step 1814, the horizontal, vertical, and/or angular position of the model face with respect to the faceplate may be adjusted based on the determined quality of the seal between the facemask and the model of the face.

At step 1816, the medication delivery from VHCs is evaluated. In one implementation, the medication delivery from VHCs is evaluated by injecting an amount of aerosolized medicine into the facemask, and measuring the total amount of aerosolized medicine received at the mouth opening of the model face. In another implementation, the medication delivery from VHCs is evaluated as before, but with the aerosol transferred from the lips of the model face to a multi-stage cascade impactor by a vacuum source attached to the impactor for the determination of aerosynamic particle size distribution.

FIGS. 1-18 teach systems and methods for evaluating the medication delivery from valved holding chambers (VHCs) with a facemask and a model face of a child or a model face of an infant. The disclosed model faces of a child and an infant simulate the soft tissues of a face so that when the model faces are mounted on a testing cradle, a facemask may be applied to the model face at a clinically appropriate orientation with an amount of clinically appropriate force. A seal between the facemask and the model face may be tested by measuring a flow rate entering the facemask and a flow rate exiting a mouth opening of the model face. Further, a medication delivery from a VHC may be evaluated by delivering aerosolized medication into the facemask and measuring an amount of medication received at the mouth opening of the model face.

It is intended that the foregoing detailed description be regarded as illustrative rather than limiting, and that it be understood that it is the following claims, including all equivalents, that are intended to define the spirit and scope of this invention.

The invention claimed is:

1. A model face for use in an evaluation of medication delivery, the model comprising:
   a base;
   an elastomer cast positioned on at least a portion of a top of the base, the elastomer simulating soft tissues in a face and defining at least a nose, a chin, and a mouth sized to simulate a nose, a chin, and a mouth of a child;
   an air pocket positioned between the base and the elastomer cast, the air pocket positioned below at least the nose, the chin, and the mouth of the elastomer cast, wherein the air pocket assists the elastomer cast in simulating soft tissues around at least the nose, the chin, and the mouth; and
   a mouth opening defining a passageway through the base, the air pocket, and the mouth of the elastomer cast, the mouth opening operative to be coupled with an induction port.

2. The model of claim 1, wherein the child is an infant.

3. The model of claim 1, wherein the mouth opening is operative to receive a flow meter.

4. The model of claim 1, wherein the mouth opening is operative to receive a pressure measurement device.

5. The model of claim 1, wherein the base defines a pair of eyes and a brow, and wherein the elastomer cast defines a pair of cheeks.

6. The model of claim 5, wherein:
   a distance between a center of a first eye of the pair of eyes and a center of a second eye of the pair of eyes is substantially 2.62 inches;
   a distance between a center of a first cheek of the pair of cheeks and a center of a second cheek of the pair of cheeks is substantially 2.94 inches;
   a distance from a center of the chin to a center of the brow is substantially 3.6 inches;
   a height of the model is substantially 4.74 inches;
   a width of the model is substantially 34.6 inches;
   a height of the mouth opening is substantially 1.66 inches; and
   a width of the mouth opening is substantially 0.88 of an inch.

7. The model of claim 5, wherein:
   a distance between a center of a first eye of the pair of eyes and a center of a second eye of the pair of eyes is substantially 2.0 inches;
   a distance between a center of a first cheek of the pair of cheeks and a center of a second cheek of the pair of cheeks is substantially 2.42 inches;
   a distance from a center of the chin to a center of the brow is substantially 2.45 inches;
   a height of the model is substantially 3.76 inches;
   a width of the model is substantially 3.86 inches;
   a height of the mouth opening is substantially 1.16 inches; and
   a width of the mouth opening is substantially 0.80 of an inch.

8. The model of claim 1, wherein the elastomer cast comprises a Shore hardness of 10.

9. The model of claim 1, wherein the air pocket comprises a depth of 0.125 inches.

10. The model of claim 1, wherein the induction port is a USP/Ph.Eur induction port.

11. A cradle for use with a model face in an evaluation of medical delivery of a valved holding chamber, the stand comprising:
   a face plate fixed at a base, the faceplate operative to mount a model face;
   an induction port in communication with the face place, the induction port operative to be coupled with a mouth opening of the model face mounted on the face plate;
   a support stand pivotly fixed at the base, the support stand operative to pivot towards the face plate;
   a cage positioned on the support stand operative to receive a facemask; and
   a weight, operative to create a force to pull the cage and support stand toward the face plate, wherein when the cage and support stand are pulled towards the face plate, a facemask in communication with the cage engages the model face mounted on the face plate.

12. The cradle of claim 11, wherein the model face comprises:
   a base;
   an elastomer cast positioned on at least a portion of a top of the base, the elastomer simulating soft tissues in a face and defining at least a nose and a chin sized to simulate a nose, a chin, and a mouth of a child;
   an air pocket positioned between the base and the elastomer cast, the air pocket positioned below at least the nose and the chin of the elastomer cast; and
   a mouth opening defining a passageway through the base, the elastomer cast, and the air pocket, the mouth opening operative to be coupled with an induction port.

13. The cradle of claim 12, wherein the child is an infant.

14. A method for evaluating a medication delivery of valved holding chambers (VHCs), the method comprising the steps of:
   mounting a model face of a child on a testing cradle;
   mounting a facemask on the testing cradle;
   initiating a force at the testing cradle to simulate a clinically appropriate force between the model face and the facemask, the force causing the facemask to engage the model face;
   testing a seal between the facemask and the model face based on a flow rate at the facemask and a flow rate leaving a mouth opening of the model face; and
   testing a medication delivery of the VHC based on an amount of an aerosolized medication inserted deployed in the facemask and an amount of the aerosolized medication received at the mouth opening of the model face.

15. The method of claim 14, wherein the child is an infant.

16. The method of claim 14, wherein the model face comprises:

a base;

an elastomer cast positioned on at least a portion of a top of the base, the elastomer simulating soft tissues in a face and defining at least a nose and a chin sized to simulate a nose, a chin, and a mouth of a child;

an air pocket positioned between the base and the elastomer cast, the air pocket positioned below at least the nose and the chin of the elastomer cast; and a mouth opening defining a passageway through the base, the elastomer cast, and the air pocket, the mouth opening operative to be coupled with an induction port.

* * * * *